US00PP29642P2

(12) United States Plant Patent
Hansen

(10) Patent No.: US PP29,642 P2
(45) Date of Patent: Sep. 4, 2018

(54) **X *MANGAVE* PLANT NAMED 'SILVER FOX'**

(50) Latin Name: **x *Mangave* x *Agave***
Varietal Denomination: Silver Fox

(71) Applicant: Hans A. Hansen, Zeeland, MI (US)

(72) Inventor: Hans A. Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 15/732,109

(22) Filed: Sep. 19, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Annette H Para

(57) ABSTRACT

A new and unique X *Mangave* plant named 'Silver Fox' characterized by a compact mound of short, broad, fleshy, heavily glaucous, foliage developing smoky purple spots and stripes in ultraviolet light. Marginal teeth are large with short sharp terminal spines. Yellow flowers are borne on large, tall, stiffly-upright, heavily-branched panicles. 'Silver Fox' is suitable for the garden landscape or as a potted plant around the garden or in the home.

2 Drawing Sheets

Botanical classification: hybrid; x *Mangave* times *Agave*.
Variety denomination: 'Silver Fox'.

BACKGROUND OF THE INVENTION

The present invention relates to the new and distinct X *Mangave* hybrid plant, X *Mangave* 'Silver Fox' hybridized by the inventor at a wholesale perennial nursery in Zeeland, Mich., USA as cross between X *Mangave* 'Bloodspot' (not patented) as the female or seed parent times a selection of *Agave gypsophila* (not patented) as the male or pollen parent. The cross was performed on Dec. 26, 2011 and seeds were harvested on Apr. 1, 2012 and sown later on Aug. 8, 2012. Through trials at the same nursery the plant was originally assigned the breeder code XMANG-12-3-39. The new plant has been successfully asexually propagated initially by division at the same nursery in Zeeland, Mich. and also by sterile shoot-tip tissue culture. Both methods of asexual propagation systems have been found to produce stable and identical plants that maintain all the unique characteristics of the original plant.

No plants of X *Mangave* 'Silver Fox' have been sold, under this or any name, in this country or anywhere in the world, prior to the filing of this application, nor has any disclosure of the new plant been made prior to the filing of this application with the exception of that which was disclosed or sold within one year of the filing of this application, and was either derived directly or indirectly from the inventor.

BRIEF SUMMARY OF THE INVENTION

X *Mangave* 'Silver Fox' differs from its parents as well as all other *Manfreda, Agave* and X *Mangave* known to the applicant. Compared with the female parent the foliage of the new plant is broader, more densely spotted with purple, more arching downward with larger marginal teeth and the flowers are yellowish. Compared with the male parent the new plant has dense purple spotting on the foliage. The most similar known cultivars are X *Mangave* 'Catch a Wave' U.S. Plant patent application Ser. No. 15/732,107, and X *Mangave* 'Tooth Fairy' U.S. Plant patent application Ser. No. 15/732,108. Compared with 'Catch a Wave' the new plant has flatter leaves that have a more glaucous blue overtone. Compared to 'Tooth Fairy' the new plant has more arching leaves with more glaucous blue overtone, and the marginal teeth are more glaucous blue colored and not as large.

The new plant, 'Silver Fox', is unique from all of the above cultivars and all *Agave*, X *Mangave* and *Manfreda* known to the inventor by the following combined traits:

1. Compact mound of short, broad, fleshy, heavily glaucous foliage;
2. Foliage develops light, irregular, smoky purple with typically-overlapping purple-lavender spots and stripes throughout upper surface;
3. Marginal teeth on leaves are large with short, sharp, terminal spines;
4. Moderate growth rate.
5. Flowers are yellowish, borne in tall, upright scapes.

BRIEF DESCRIPTION OF THE DRAWING

The photograph of x *Mangave* 'Silver Fox' demonstrates the overall appearance of the new plant including the unique traits as a two-year-old plant grown in a container in a greenhouse with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
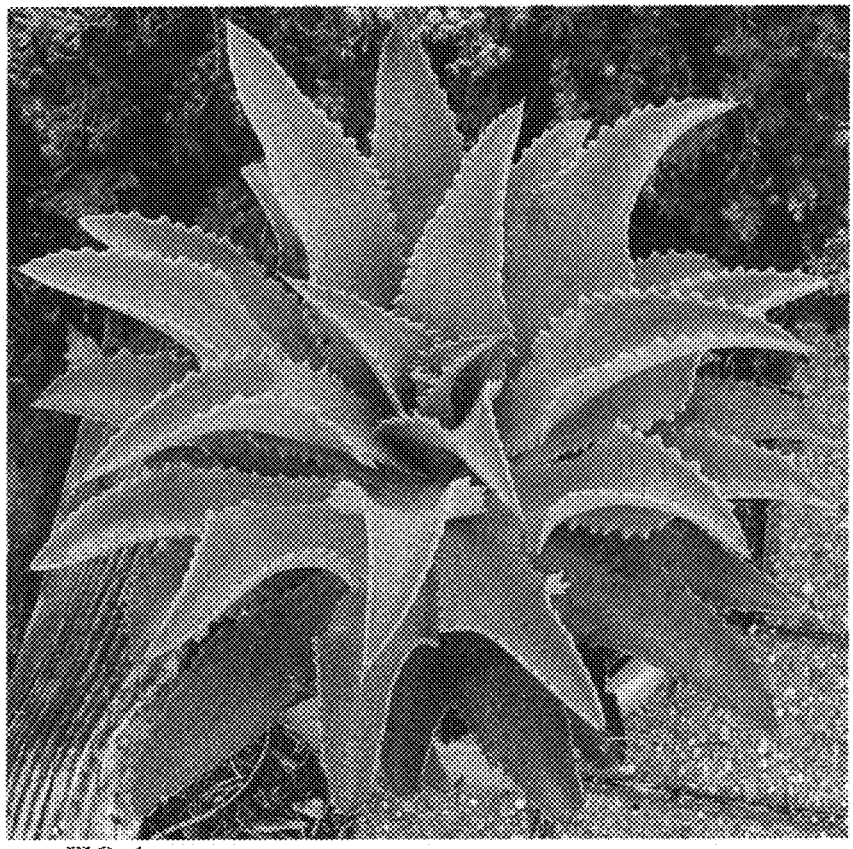
FIG. 1 shows the new plant grown in a container with foliage color changes, teeth and apical spines.
Figure 2:
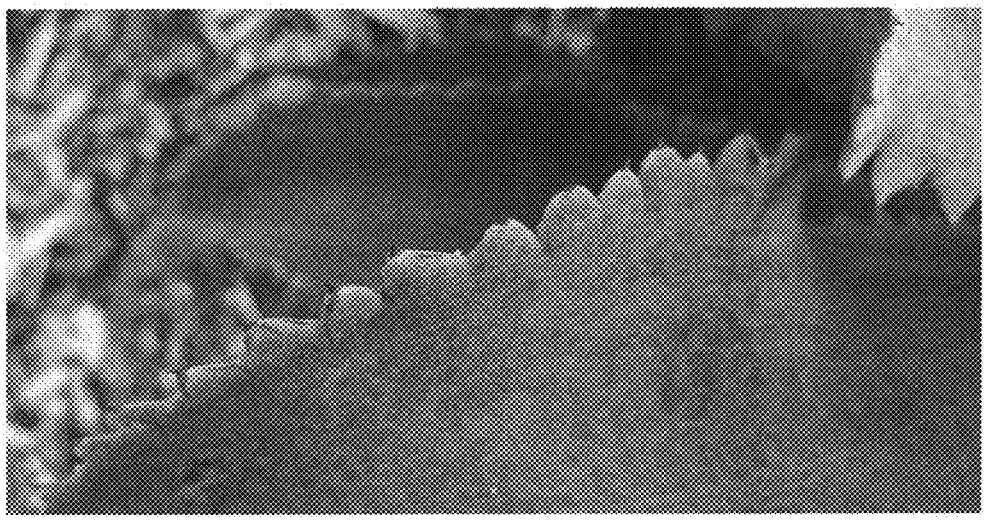
FIG. 2 shows a close-up of the leaf with irregular purple markings and marginal teeth.
Figure 3:
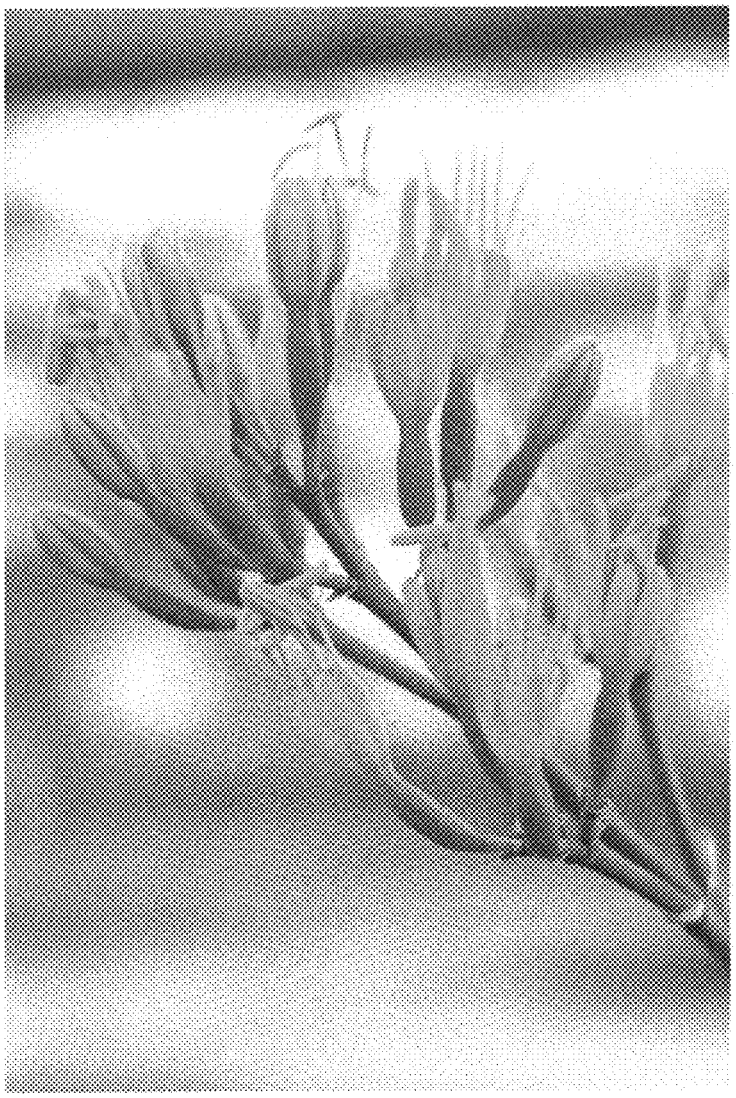
FIG. 3 shows a close-up of the flowers and buds.

The following descriptions and color references are based on the 2015 edition of The Royal Horticultural Society Colour Chart except where common dictionary terms are used. The new plant, X *Mangave* 'Silver Fox', has not been observed under all possible environments. The phenotype may vary slightly with different environmental conditions, such as temperature, light, fertility, moisture and maturity levels, but without any change in the genotype. The following observations and size descriptions are of a two-year old plant in a commercial wholesale greenhouse and also in a full-sun display garden in Zeeland, Mich. with supplemental water and fertilizer as needed.

Parentage: X *Mangave* 'Bloodspot' as the female (seed) patent and *Agave gypsophila* as the male (pollen) parent;

Propagation: Division of side shoots and sterile shoot-tip tissue culture;

Time to initiate roots from tissue culture: About 21 days;

Growth rate: Moderate; faster than typical *agave;*

Crop time: About 14 to 18 weeks to finish in a 3.8 liter container from a 35 mm tissue culture growing at about 24° C.;

Rooting habit: Fleshy, lightly branching, with roots up to 30.0 cm long;

Root color: Nearest RHS 158C;

Plant shape and habit: Succulent herbaceous perennial with basal rosettes of about 50 leaves radially emerging outwardly from central stem, producing a radially-symmetrical, rounded mound;

Plant size: Foliage height about 25.0 cm tall from soil line to the top of the leaves and about 50.0 cm wide at the widest point slightly below soil line in container at time of flowering;

Foliage description: Lanceolate; arcuate distally; simple; margins coarsely dentate with short stiff spines, thick and fleshy; teeth about 4.0 mm long and spaced average of about 10.0 mm apart; apex acute with terminal spine about 6.0 mm long; base truncate and slightly attenuate; sessile; slightly longitudinally conduplicate; bi-laterally symmetrical; with irregular purple spots and stripes; about 48 leaves per plant below scape;

Leaf size: To about 24.0 cm long, about 6.5 cm wide approximately two-thirds toward apex and about 12.0 mm thick at middle base; average about 23.0 cm long, 6.0 cm wide and 10.0 mm thick;

Foliage fragrance: None observed;

Leaf blade color:

*Adaxial* (*outdoor garden*).—Nearest RHS N187C with irregular spots and stripes intensifying with ultraviolet light exposure to nearest RHS N187A; Abaxial (outdoor): nearest RHS 189B without noticeable spots.

*Adaxial* (*greenhouse*).—Blend between RHS 188B and RHS 191B with spots and stripes intensifying with ultraviolet light exposure closer to RHS N187B than RHS N187A.

*Abaxial* (*greenhouse*).—Nearest RHS 189C.

Teeth spine color: Base nearest RHS 175A and apex becoming nearest RHS 200A;

Petiole: Leaves sessile;

Veins: Parallel; not distinct abaxial or adaxial;

Inflorescence: Stiff, upright panicle; glaucous; terete; heavily branched with average about 28 primary branches per plant; up to 41 flowers per primary branch, decreasing distally; to about 330 cm long and about 2.5 cm diameter at base; with about 27 foliar bracts before flowers; flowering portion to about 220.0 cm tall and 75.0 wide;

Panicle branches: To about 30.0 cm long and 8.0 mm diameter at base, decreasing distally; upwardly and slightly outwardly;

Peduncle color: Base and middle portion between RHS N187A and RHS N187B with an undertone of nearest RHS 138A, upper portion and branches between RHS 138A and RHS 138B with tinting of nearest RHS 187A;

Pedicle: Terete; glabrous, slightly glaucous; about 8.5 mm long and 3.0 mm diameter;

Pedicle color: Nearest RHS 138B;

Flower description: Perfect; actinomorphic; uprightly; 4.6 cm long and 3.0 cm wide to exserted anthers; style lengthening with age;

Flower fragrance: Very faint to not detectable;

Tepals: Two sets of three; glabrous abaxial and adaxial; fused in basal 9.0 mm; with acute apex; 15.0 mm total length; inner set about 5.0 mm wide just above fusion, outer set about 4.0 mm wide;

Tepal color: Abaxial base nearest RHS 11A, abaxial apex nearest RHS 22A; adaxial base nearest RHS 13A and adaxial apex nearest RHS 22A;

Androecium: Six; exserted beyond tepals; adnate to adaxial tepal base;

*Filaments*.—To about 30.0 mm long and 1.5 mm diameter at base; color nearest RHS 4D at the base and nearest RHS 2B distally.

*Anthers*.—Basifixed; longitudinal; oblong with rounded apices; to about 13.0 mm long and 2.5 mm across; color between RHS 15A and RHS 17C.

*Pollen*.—Abundant; color nearest RHS 17B.

Gynoecium: To about 4.4 cm long when fully developed;

*Ovary*.—Inferior; oblong; about 15.0 mm long and 5.0 mm across in middle; color nearest RHS 138A.

*Style*.—Elongating with maturity to about 2.8 cm long and 2.0 mm diameter at base; color nearest RHS 4D at the base and nearest RHS 2B distally.

*Stigma*.—Flat-topped to about 3.5 mm across; color nearest RHS 15A.

Fruit: Tri-valved loculicidal capsule; oblong; about 2.5 cm long and about 1.5 cm across, with acute apex and rounded base; color between RHS 199D and RHS 161D when mature;

Seed: Dried; flattened; about 6.0 mm long, about 5.0 mm across and about 1.0 mm thick; color nearest RHS 202A;

Disease resistance: X *Mangave* 'Silver Fox' has not been observed to be resistant to diseases beyond that which is normal for X *Mangave, Agave* or *Manfreda*. The new plant is xeromorphic and survives well with minimal water once established. The new plant is hardy at least in USDA zone 10. Full extent of winter hardiness has not been tested.

It is claimed:

1. A new and distinct cultivar of ornamental X *Mangave* plant named 'Silver Fox' as herein described and illustrated.

* * * * *